United States Patent
Kutzko et al.

(10) Patent No.: US 6,942,614 B1
(45) Date of Patent: *Sep. 13, 2005

(54) METHOD AND SYSTEM FOR USE IN TREATING A PATIENT WITH AN ANTICOAGULANT TO OPTIMIZE THERAPY AND PREVENT AN ADVERSE DRUG RESPONSE

(75) Inventors: John D. Kutzko, Nokomis, FL (US); Michaeal G. Singer, Harrisville, MI (US); John McMichael, Wexford, PA (US)

(73) Assignee: Dimensional Dosing Systems, Inc., Wexford, PA (US)

(*) Notice: Subject to any disclaimer, the term of this patent is extended or adjusted under 35 U.S.C. 154(b) by 856 days.

This patent is subject to a terminal disclaimer.

(21) Appl. No.: 09/644,503

(22) Filed: Aug. 24, 2000

Related U.S. Application Data

(63) Continuation-in-part of application No. 09/348,592, filed on Jul. 6, 1999, now Pat. No. 6,267,116.

(51) Int. Cl.[7] .......................... A61B 5/00; A61B 19/00; G06F 17/00
(52) U.S. Cl. .......................... 600/300; 128/898; 700/90
(58) Field of Search .......................... 700/90; 128/897, 128/898; 600/300, 308, 347, 364–366, 368, 369

(56) References Cited

U.S. PATENT DOCUMENTS

| | | | |
|---|---|---|---|
| 5,365,948 A | | 11/1994 | McMichael |
| 5,542,436 A | | 8/1996 | McMichael |
| 5,694,950 A | | 12/1997 | McMichael |
| 6,267,116 B1 | * | 7/2001 | McMichael .................. 128/898 |
| 6,575,169 B2 | * | 6/2003 | McMichael .................. 128/898 |
| 6,581,606 B2 | * | 6/2003 | Kutzko et al. .............. 128/898 |
| 6,581,607 B2 | * | 6/2003 | Kutzko et al. .............. 128/898 |

* cited by examiner

*Primary Examiner*—Leo Picard
*Assistant Examiner*—Ryan Jarrett
(74) *Attorney, Agent, or Firm*—Gifford, Krass, Groh, Sprinkle, Anderson & Citkowski, P.C.

(57) ABSTRACT

A method and system for use in treating a patient receiving an anticoagulant or a substance containing warfarin to optimize therapy and prevent an adverse drug response. This system employs surrogate markers or indicators including blood levels of the anticoagulant to determine the next required dose for a patient. Since the surrogate markers are employed as a percent change in status, virtually any indicator can be used. Surrogate markers could include any measure of the effectiveness of the anticoagulant's action. Given the effectiveness of the anticoagulant's action relative to the surrogate markers, a change in anticoagulant dose is calculated by the system. Conversely, by employing this system, one could determine the expected result of the anticoagulant dose change on the surrogate markers.

50 Claims, 2 Drawing Sheets

METHOD AND SYSTEM FOR USE IN TREATING A PATIENT WITH AN ANTICOAGULANT TO OPTIMIZE THERAPY AND PREVENT AN ADVERSE DRUG RESPONSE

RELATED APPLICATION

The present patent application is a continuation-in-part of U.S. patent application Ser. No. 09/348,592 filed on Jul. 6, 1999 now U.S. Pat. No. 6,267,116, the entire contents of which are incorporated herein by reference thereto.

This document may contain material which is the subject of copyright protection. All rights in such copyrightable material are hereby reserved.

FIELD OF THE INVENTION

The present invention relates generally to a method and system for use in, treating a patient with an anticoagulant to optimize drug therapy and to prevent an adverse drug response. More particularly, the present invention relates to a method and system for use in treating a patient with Coumadin® or a substance containing warfarin. The present invention can utilize either drug levels or other surrogate markers to determine the effectiveness of the dosing regimen and, if necessary, to suggest a new more optimal drug dose.

The term "anticoagulant" as used herein includes, but is not limited to, warfarin, Coumadin®, heparin, warfarin sodium salt, coumarin derivatives, indandione derivatives, dicumarol, anisindione, phenindione, ethyl bicoumacetate, bishydroxycoumarin, abcimixab, Reopro®, actilyse, alteplase, Activase®, anagrelide, Agrylin®, anistreplase, Eminase®, antithrombin III, Thrombate III®, ardeparin, Normiflo®, argatroban, clopidrogel, Plavix®, dalteparin, Fragmin®, danaparoid, Orgaran®, dipyridamole, Persantine®, dipyridamole/aspirin, Aggrenox®, duteplase, enoxaparin, Lovenox®, eptifibatide, Integrilin®, lepirudin, Refludan®, nadroparin, Fraxiparine®, oprelvekin, Neumega®, pentosan polysulfate sodium, Elmiron®, reteplase, Retavase®, reviparin, Clivarine®, saruplase, streptokinase, Kabikinase®, Streptase®, tinzaparin, Innohep®, tirofiban, Aggrastat®, unfractionated heparin, low molecular weight heparin, all antithrombotic agents, all vitamin K antagonists, and all substances derived from and/or related to the foregoing substances.

Furthermore, wherever the generic term "anticoagulant" is used herein it is also intended to mean species which employ any or more of the individual anticoagulants as defined and/or alluded to hereinabove.

BACKGROUND OF THE INVENTION

When a patient begins taking an anticoagulant or any medication for a length of time, a titration of the amount of drug taken by the patient is necessary in order to achieve the optimal benefit of the drug, and at the same time to prevent any undesirable side effects that taking too much of the drug could produce. Thus, there is a continuous balance between taking enough drug in order to gain the benefits from that drug and at the same time not taking so much drug as to illicit a toxic event.

There is large inter-individual variability in the patient pharmacodynamic and pharmacokinetic interactions of drugs. What may be an appropriate drug dose for one individual, may be too much or too little for another. Prior to this invention a physician was required to estimate the correct drug dosage for a patient and then to experiment with that dosage, usually by trial and error, until the correct dosage was achieved. Likewise, the FDA labeling of a drug suggests dosages based on epidemiological studies and again does not account for inter-individual variability. Non-linear least squares modeling methods involve the use of large amounts of data relating to a general population in order to calculate a best fit. Much like linear regression models, this method cannot take into account the variability between people with the same population characteristics.

Bayesian analysis is another method used to relate drug dose to efficacy. This method employs large-scale population parameters to stratify a population in order to better characterize the individuals. This method does not take into account the changes that can occur within a person over time, and as a result cannot reliably estimate dosages.

Pharmacokinetic compartment modeling has had success with some drugs, but because the models are static and cannot adapt themselves to changes within a population or a patient, they are once again undesirable for dynamically determining drug dosages.

Expert systems have been developed using similar technology to predict drug dosages for immunosuppressant drugs (see, e.g., U.S. Pat. Nos. 5,365,948, 5,542,436 and 5,694,950). These algorithms, however, are not generic and only use immunosuppressant blood levels. Each algorithm is specific to an individual immunosuppressant drug. As it stands, these inventions cannot be applied to other drugs and do not have a non-linear feedback loop mechanism.

SUMMARY OF THE INVENTION

According to the present invention, patient dosing occurs through a cyclic series of events, depicted in flow chart form in FIG. 1. After an initial examination, an initial dose of a drug, such as an anticoagulant, is prescribed and administered by a physician for a patient. The initial dose is based on the FDA recommended dosage found on the drug label. The anticoagulant dose is further refined upon repeated dosing by the physician based on the patient's response to the anticoagulant. Too much anticoagulant could cause the patient to experience toxic anticoagulant effects, and the anticoagulant dose would need to be reduced. Too little anticoagulant could cause the patient not to receive the benefit the anticoagulant therapy could offer, and the dosage would need to be increased.

The preferred embodiment of the invention requires that a physician determine the percentage of response by the patient to the anticoagulant based on the surrogate markers for that anticoagulant. A relationship is then employed which uses the input parameters described above to determine the next dose for the patient.

The invention also includes embodiments focused on specific anticoagulants, such as, for example only, Coumadin®, warfarin, substances containing warfarin, etc. For example, the invention includes a method for calculating a revised dose of Coumadin® for a patient using Coumadin®, comprising the steps of: accepting as a first input the patient's current Coumadin® dose; accepting as a second input a maximum dose of Coumadin®; accepting as a third input a percent response of the patient based on one or more surrogate markers for said patient; and determining a revised dose, wherein said revised dose is a function of said current dose minus a ratio of the percent response of the patient and a ratio of said current dose to said maximum dose plus the percent of individual patient response multiplied by a response factor.

Another example is a method for determining a dose of warfarin or a substance containing warfarin for a patient, comprising the steps of: administering an initial dose of Warfarin or said substance containing warfarin to the patient; examining the patient to monitor and characterize one or more numerical surrogate markers; determining if a dose change is necessary; and calculating a revised dose as a function of said current dose minus the ratio of the change in numerical markers and the ratio of said current dose to said maximum dose plus the percent of individual patient response multiplied by a response factor.

Each specie of the invention has two preferred embodiments; one which uses actual numerical surrogate markers to calculate a dose, and another embodiment that uses percentages as the numerical input for the surrogate markers.

DETAILED DESCRIPTION OF THE INVENTION

The present invention provides a method and system for use in treating a patient receiving an anticoagulant or a substance containing warfarin to optimize therapy and to prevent an adverse drug response. This system employs surrogate markers or indicators including blood levels of the anticoagulant to determine the next required dose for a patient. Because the surrogate markers are employed as a percent change in status, virtually any indicator can be used. Surrogate markers could include any measure of the effectiveness of the anticoagulant's action. Given the effectiveness of the anticoagulant's action relative to the surrogate markers, a change in anticoagulant dose is calculated by the system. Conversely, by employing this system, one could determine the expected result of the anticoagulant dose change on the surrogate markers.

Figure 1:
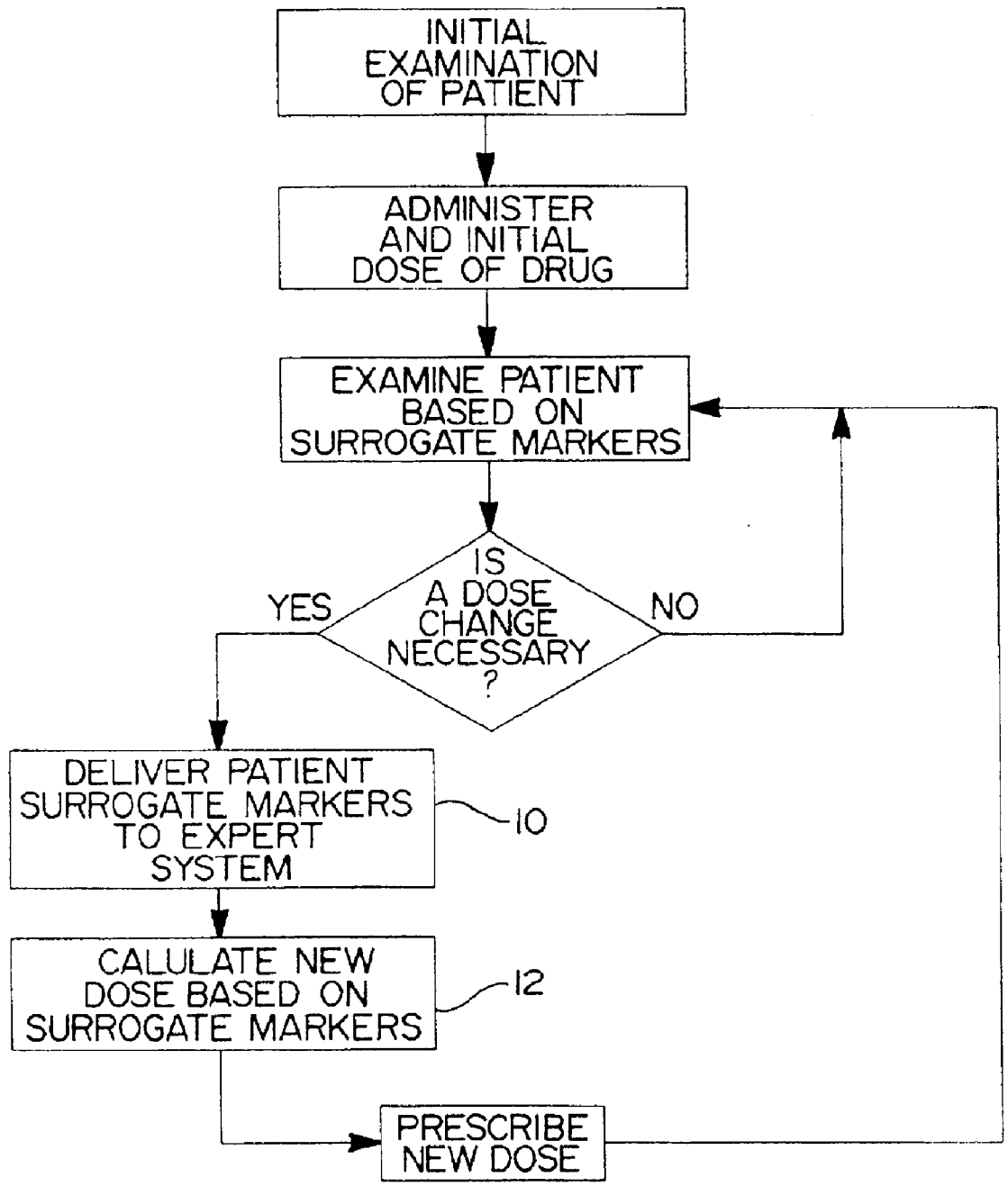
FIG. 1 shows a flow chart of the process by which revised doses of an anticoagulant are determined, according to the method of the invention described herein.
Figure 2:
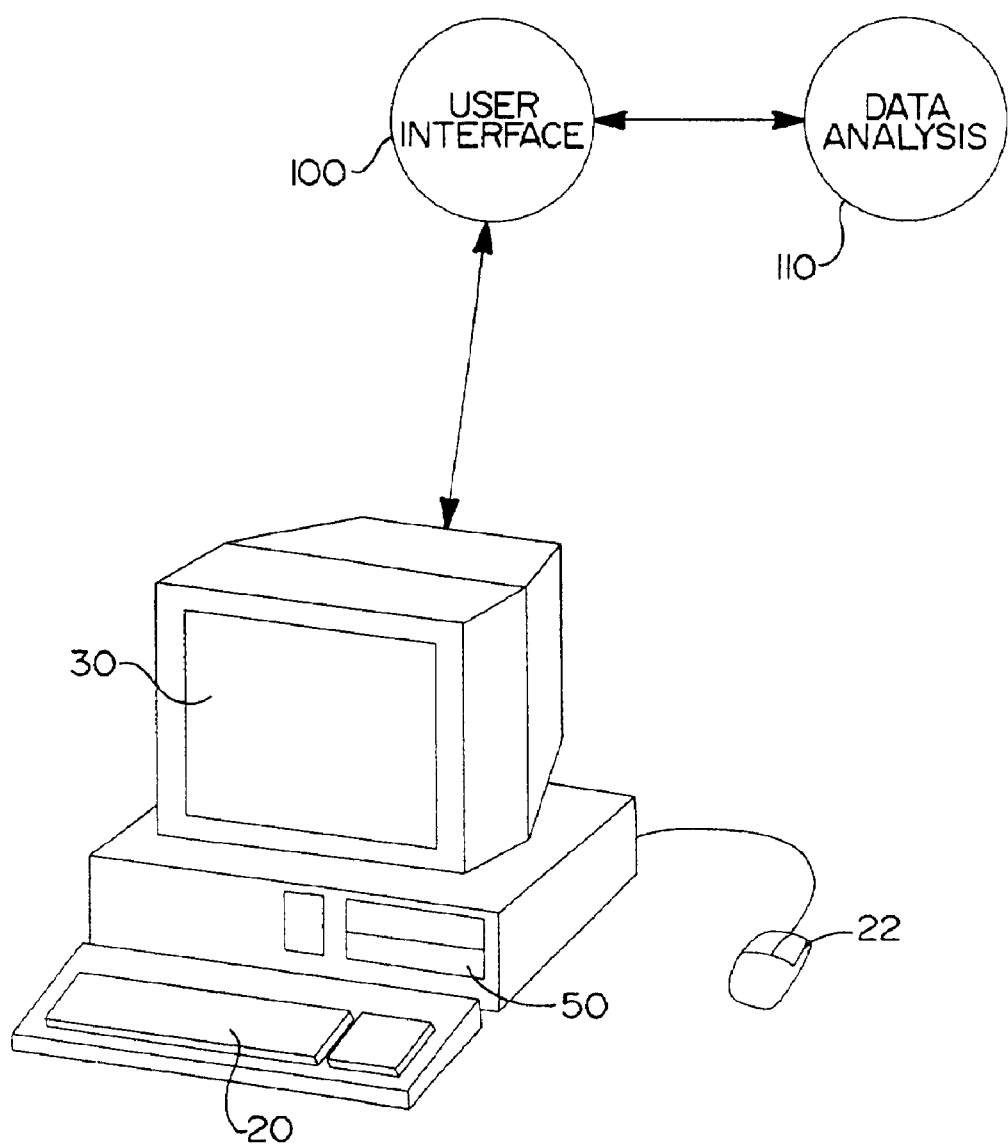
FIG. 2 shows an apparatus for use in calculating revised doses of an anticoagulant according to the present invention.

This expert system includes a general purpose computer, shown in FIG. 2, comprising an input means, preferably a keyboard 20 and/or a mouse 22, an output means 30, preferably a video display screen, a data storage means 50, preferably a hard disk drive, and a processor. The expert computer program receives input data from a physician regarding the patient's current anticoagulant dose, the maximal dose range for the anticoagulant, and the percent response of the patient based on the surrogate markers used to monitor the anticoagulant. Also characterized is the patient's response to the last dosing cycle as well as a dose response constant. This allows the expert system to individualize the patient dosing based on the patient's individual response to the anticoagulant. The system calculates a revised dosage based on the data input by the physician. The software portion of the invention includes a user interface portion 100 to receive the input data and to output the revised dosage information, and a data analysis portion 110, which calculates the new dosage information based on the input data.

Numerical Surrogate Markers Embodiment

A physician prescribes an anticoagulant for a patient based on the FDA recommended dose on the label of the anticoagulant. The physician then re-evaluates the patient, usually daily, either in person or remotely depending on the agent being prescribed. During the subsequent evaluations by the physician, the surrogate markers are monitored and sequentially compared to determine if there are any toxicities associated with the anticoagulant. Also the numerical markers will evaluated to see if the desired effect of the anticoagulant is being achieved. Based on this evaluation by the physician, the current anticoagulant dose, the current anticoagulant numerical marker, the desired anticoagulant numerical marker, and the previous anticoagulant numerical marker are then input into the embodiment and the new anticoagulant dose is calculated based on the equation:

$$NAD=CAD-\{[<(CANM-DANM)/CANM>/<1+(CAD/HIGH)>]\times CAD\}+LV$$

where:
  $LV=\{(RESPONSE \times CAD) \times [(1+D)-(1+E)]/abs(1+D)\}/1.3^{\wedge}(CAD/HIGH)$
  $E=CANM-PANM$
  $D=DANM-PANM$
and wherein:
  NAD=New Anticoagulant Dose
  CAD=Current Anticoagulant Dose
  CANM=Current Anticoagulant Numerical Marker
  DANM=Desired Anticoagulant Numerical Marker
  PANM=Previous Anticoagulant Numerical Marker
  HIGH=The input parameter that is the high dose range for said anticoagulant
  RESPONSE=Percent of total dose available for individualizing patient dose
  abs=The absolute value of $1.3^{\wedge}(CAD/HIGH)=1.3$ raised to an exponent of (CAD/HIGH).

Percentage Surrogate Markers Embodiment

In this preferred embodiment, a physician prescribes an anticoagulant for a patient based on the FDA recommended dose on the label of the anticoagulant The physician then re-evaluates the patient, usually daily, either in person or remotely depending on the agent being prescribed. During the subsequent evaluations by the physician, the surrogate markers are monitored and sequentially compared to determine if there are any toxicities associated with the anticoagulant. Also the surrogate markers are evaluated to see if the desired effect of the anticoagulant is being achieved. Based on this evaluation by the physician, the current anticoagulant dose, and the percent response of the patient to the last dosing based on a surrogate marker are then input into the system and the new anticoagulant dose is calculated based on the equation:

$$NAD=CAD-\{[<(PAR-100)/PAR>/<1+(CAD/HIGH)>]\times CAD\}+LV$$

where:
  $LV=\{(RESPONSE \times CAD) \times [(100-RES) \times 0.01]\}/1.3^{\wedge}(CAD/HIGH)$
and wherein:
  NAD=New Anticoagulant Dose
  CAD=CurrentAnticoagulant Dose
  PAR=Percent response of patient to surrogate marker
  RES=Percent response of patient to last dosing based on surrogate marker
  HIGH=The input parameter that is the high dose range for said anticoagulant
  RESPONSE=Percent of total dose available for individualizing patient dose
  $1.3^{\wedge}(CAD/HIGH)=1.3$ raised to an exponent of (CAD/HIGH).

This cycle of repeated re-evaluation of the numerical surrogate markers is continued as long as the patient is required to take the anticoagulant.

Two embodiments of the invention have been described, one using numerical markers, and one using a percentage surrogate marker.

Although the invention has been described in detail in the foregoing for the purpose of illustration, it is to be understood that such detail is solely for that purpose and that variations can be made therein by those of ordinary skill in the art without departing from the spirit and scope of the invention as defined by the following claims, including all equivalents thereof.

What is claimed is:

1. A method for calculating a revised dose of an anticoagulant for a patient using said anticoagulant, comprising the steps of:

accepting as a first input the patient's current anticoagulant dose;

accepting as a second input a maximum dose of the anticoagulant;

accepting as a third input a percent response of the patient based on one or more surrogate markers for said patient; and determining a revised dose, wherein said revised dose is a function of said current dose minus a ratio of the percent response of the patient and a ratio of said current dose to said maximum dose plus the percent of individual patient response multiplied by a response factor.

2. The method of claim 1, wherein:

said determining step includes determining said revised dose based on the equation $$RAD=CAD-\{[<(PAR-100)/PAR>/<1+(CAD/HIGH)>] \times CAD\}+LV$$

where:

$LV=\{(RESPONSE \times CAD) \times [(100-RES) \times 0.01]\}/1.3^{\wedge}(CAD/HIGH)$ and wherein:

RAD=Revised Anticoagulant Dose
CAD=Current Anticoagulant Dose
PAR=Percent response of patient to surrogate marker
RES=Percent response of patient to last dosing based on surrogate marker
HIGH=The input parameter that is the high dose range for said anticoagulant
RESPONSE=Percent of total dose available for individualizing patient dose
$1.3^{\wedge}(CAD/HIGH)=1.3$ raised to an exponent of (CAD/HIGH).

3. The method of claim 1, wherein: said anticoagulant is selected from a group comprising warfarin, Coumadin®, heparin, warfarin sodium salt, coumarin derivatives, indandione derivatives, dicumarol, anisindione, phenindione, ethyl bicoumacetate, bishydroxycoumarin, abcimixab, Reopro®, actilyse, alteplase, Activase®, anagrelide, Agrylin®, anistreplase, Eminase®, antithrombin III, Thrombate III®, ardeparin, Normiflo®, argatroban, clopidrogel, Plavix®, dalteparin, Fragmin®, danaparoid, Organan®, dipyridamole, Persantine®, dipyridamole/aspirin, Aggrenox®, duteplase, enoxaparin, Lovenox®, eptifibatide, Integrilin®, lepirudin, Refludan®, nadroparin, Fraxiparine®, oprelvekin, Neumega®, pentosan polysulfate sodium, Elmiron®, reteplase, Retavase®, reviparin, Clivarine®, saruplase, streptokinase, Kabikinase®, Streptase®, tinzaparin, Innohep®, tirofiban, Aggrastat®, unfractionated heparin, low molecular weight heparin, all antithrombotic agents, all vitamin K antagonists, and all substances derived from and/or related to the foregoing substances.

4. A method for calculating a revised dose of a anticoagulant for a patient using said anticoagulant comprising the steps of:

accepting as a first input the patient's current anticoagulant dose;

accepting as a second input a maximum dose of the anticoagulant;

accepting as a third input one or more numerical markers indicating a response of the patient; and calculating said revised dose, wherein said revised dose is a function of said current dose minus the ratio of the change in numerical markers and the ratio of said current dose to said maximum dose plus the percent of individual patient response multiplied by a response factor.

5. The method of claim 4, wherein:

said calculating step includes calculating said revised dose based on the equation $$RAD=CAD-\{[<(CANM-DANM)/CANM>/<1+(CAD/HIGH)>] \times CAD\}+LV$$

where:

$LV=\{(RESPONSE \times CAD) \times [(1+D)-(1+E)]/abs\ (1+D)\}/1.3^{\wedge}(CAD/HIGH)$
$E=CANM-PANM$
$D=DANM-PANM$ and wherein:

RAD=Revised Anticoagulant Dose
CAD=Current Anticoagulant Dose
CANM=Current Anticoagulant Numerical Marker
DANM=Desired Anticoagulant Numerical Marker
PANM=Previous Anticoagulant Numerical Marker
HIGH=The input parameter that is the high dose range for said anticoagulant
RESPONSE=Percent of total dose available for individualizing patient dose
abs=The absolute value of
$1.3^{\wedge}(CAD/HIGH)=1.3$ raised to an exponent of (CAD/HIGH).

6. The method of claim 4, wherein:

said anticoagulant is selected from a group comprising warfarin, Coumadin®, heparin, warfarin sodium salt, coumarin derivatives, indandione derivatives, dicumarol, anisindione, phenindione, ethyl bicoumacetate, bishydroxycoumarin, abcimixab, Reopro®, actilyse, alteplase, Activase®, anagrelide, Agrylin®, anistreplase, Eminase®, antithrombin III, Thrombate III®, ardeparin, Normiflo®, argatroban, clopidrogel, Plavix®, dalteparin, Fragmin®, danaparoid, Organan®, dipyridamole, Persantine®, dipyridamole/aspirin, Aggrenox®, duteplase, enoxaparin, Lovenox®, eptifibatide, Integrilin®, lepirudin, Refludan®, nadroparin, Fraxiparine®, oprelvekin, Neumega®, pentosan polysulfate sodium, Elmiron®, reteplase, Retavase®, reviparin, Clivarine®, saruplase, streptokinase, Kabikinase®, Streptase®, tinzaparin, Innohep®, tirofiban, Aggrastat®, unfractionated heparin, low molecular weight heparin, all antithrombotic agents, all vitamin K antagonists, and all substances derived from and/or related to the foregoing substances.

7. A method for determnining a dose of a anticoagulant for a patient, comprising the steps of:

administering an initial dose of said anticoagulant to the patient;

evaluating the patient to monitor and characterize one or more numerical surrogate markers;

determining, based on said numerical surrogate markers, if a dose change for said anticoagulant is necessary; and calculating a revised dose as a function of said current dose minus the ratio of a percent response of the patient and the ratio of said current dose to a maximum dose plus the percent of individual patient response multiplied by a response factor.

8. The method of claim 7, wherein:

said anticoagulant is selected from a group comprising warfarin, Coumadin®, heparin, warfarin sodium salt, coumarin derivatives, indandione derivatives, dicumarol, anisindione, phenindione, ethyl bicoumacetate, bishydroxycoumarin, abcimixab, Reopro®, actilyse, alteplase, Activase®, anagrelide, Agrylin®, anistreplase, Eminase®, antithrombin III, Thrombate III®, ardeparin, Normiflo®, argatroban, clopidrogel, Plavix®, dalteparin, Fragmin®, danaparoid, Organan®, dipyridamole, Persantine®, dipyridamole/aspirin, Aggrenox®, duteplase, enoxaparin, Lovenox®, eptifibatide, Integrilin®, lepirudin, Refludan®, nadroparin, Fraxiparine®, oprelvekin, Neumega®, pentosan polysulfate sodium, Elmiron®, reteplase, Retavase®, reviparin, Clivarine®, saruplase, streptokinase, Kabikinase®, Streptase®, tinzaparin, Innohep®, tirofiban, Aggrastat®, unfractionated heparin, low molecular weight heparin, all antithrombotic agents, all vitamin K antagonists, and all substances derived from and/or related to the foregoing substances.

9. A method for determining a dose of an anticoagulant for a patient, comprising the steps of:

administering an initial dose of said anticoagulant to the patient;

examining the patient to monitor and characterize one or more numerical surrogate markers;

determining if a dose change is necessary; and calculating a revised dose as a function of said current dose minus the ratio of the change in numerical markers and the ratio of said current dose to the maximum dose plus the percent of individual patient response multiplied by a response factor.

10. A method for calculating a revised dose of an anticoagulant for a patient, comprising the steps of:

accepting as input the patient's current anticoagulant dose;

accepting as input a maximum dose of the anticoagulant;

accepting as input the percent response of the patient based on surrogate markers; and calculating a revised dose, wherein said revised dose is a function of said current dose, said maximum dose, and said percent response of the patient based on said surrogate markers.

11. A method for calculating a revised dose of an anticoagulant for a patient, comprising the steps of:

accepting as input a patient's current anticoagulant dose;

accepting as input a maximum dose of the anticoagulant;

accepting as input the previous, current and desired values of one or more numerical markers indicating the response of the patient; and calculating a revised dose, wherein said revised dose is a function of said current dose, said maximum dose, and said previous, current and desired values of said numerical markers.

12. A storage device having stored thereon an ordered set of instructions which, when executed by a computer, performs a method comprising the steps of:

accepting as input a patient's current anticoagulant dose;

accepting as input a maximum dose of the anticoagulant;

accepting as input a percent response of a patient based on surrogate markers; and calculating a revised dose, wherein said revised dose is a function of said current dose minus the ratio of a percent response of the patient and the ratio of said current dose to said maximum dose plus the percent of individual patient response multiplied by a response factor.

13. The storage device of claim 12, wherein:

said anticoagulant is selected from a group comprising warfarin, Coumadin®, heparin, warfarin sodium salt, coumarin derivatives, indandione derivatives, dicumarol, anisindione, phenindione, ethyl bicoumacetate, bishydroxycoumarin, abcimixab, Reopro®, actilyse, alteplase, Activase®, anagrelide, Agrylin®, anistreplase, Eminase®, antithrombin III, Thrombate III®, ardeparin, Normiflo®, argatroban, clopidrogel, Plavix®, dalteparin, Fragmin®, danaparoid, Organan®, dipyridamole, Persantine®, dipyridamnole/aspirin, Aggrenox®, duteplase, enoxaparin, Lovenox®, eptifibatide, Integrilin®, lepirudin, Refludan®, nadroparin, Fraxiparine®, oprelvekin, Neumega®, pentosan polysulfate sodium, Elmiron®, reteplase, Retavase®, reviparin, Clivarine®, saruplase, streptokinase, Kabilinase®, Streptase®, tinzaparin, Innohep®, tirofiban, Aggrastat®, unfractionated heparin, low molecular weight heparin, all antithrombotic agents, all vitamin K antagonists, and all substances derived from and/or related to the foregoing substances.

14. A storage device having stored thereon an ordered set of instructions which, when executed by a computer, performs a method comprising the steps of:

accepting as input the patient's current anticoagulant dose;

accepting as input a maximum dose of the anticoagulant;

accepting as input one or more numerical markers indicating the response of the patient; and calculating a revised dose, wherein said revised dose is a function of said current dose minus the ratio of the change in numerical markers and the ratio of said current dose to said maximum dose plus the percent of individual patient response multiplied by a response factor.

15. An apparatus for calculating a revised dose of an anticoagulant for a patient comprising:

means for accepting as input one or more markers which indicate a patient's response to a dose of said anticoagulant;

means for accepting as input the patient's current anticoagulant dose;

means for accepting as input the maximum dose of the anticoagulant; and means for calculating a revised dose of the anticoagulant as a function of said markers, said current anticoagulant dose, and said maximum anticoagulant dose.

16. The apparatus of claim 15, wherein:

said markers are actual numerical markers.

17. The apparatus of claim 15, wherein:

said markers are surrogate markers representing a percent response of the patient to the anticoagulant.

18. The apparatus of claim 15, wherein:

said revised dose is calculated by the equation:

$$RAD = CAD - \{[<(CANM-DANM)/CANM>/<1+(CAD/HIGH)<] \times CAD\} + LV$$

where:
  LV={(RESPONSE×CAD)×[(1+D)−(1+E)]/abs (1+D)}/1.3^(CAD/HIGH)
  E=CANM−PANM
  D=DANM−PANM
and wherein:
  RAD=Revised Anticoagulant Dose
  CAD=Current Anticoagulant Dose
  CANM=Current Anticoagulant Numerical Marker
  DANM=Desired Anticoagulant Numerical Marker
  PANM=Previous Anticoagulant Numerical Marker
  HIGH=The input parameter that is the high dose range for said anticoagulant
  RESPONSE=Percent of total dose available for individualizing patient dose
  abs=The absolute value of
  1.3^(CAD/HIGH)=1.3 raised to an exponent of (CAD/HIGH).

19. The apparatus of claim 15, wherein:
  said revised dose is calculated by the equation:

$$RAD=CAD-\{[<(PAR-100)/PAR>/<+(CAD/HIGH)>]\times CAD\}+LV$$

where:
  LV={(RESPONSE×CAD)×[(100−RES)×0.01]}/1.3^(CAD/HIGH)
and wherein:
  RAD=Revised Anticoagulant Dose
  CAD=Current Anticoagulant Dose
  PAR=Percent response of patient to surrogate marker
  RES=Percent response of patient to last dosing based on surrogate marker
  HIGH=The input parameter that is the high dose range for said anticoagulant
  RESPONSE=Percent of total dose available for individualizing patient dose
  1.3^(CAD/HIGH)=1.3 raised to an exponent of (CAD/HIGH).

20. The apparatus of claim 15, wherein:
  said anticoagulant is selected from a group comprising warfarin, Coumadin®, heparin, warfarin sodium salt, coumarin derivatives, indandione derivatives, dicumarol, anisindione, phenindione, ethyl bicoumacetate, bishydroxycoumarin, abcimixab, Reopro®, actilyse, alteplase, Activase®, anagrelide, Agrylin®, anistreplase, Eminase®, antithrombin III, Thrombate III®, ardeparin, Normiflo®, argatroban, clopidrogel, Plavix®, dalteparin, Fragmin®, danaparoid, Organan®, dipyridamole, Persantine®, dipyridamole/aspirin, Aggrenox®, duteplase, enoxaparin, Lovenox®, eptifibatide, Integrilin®, lepirudin, Refludan®, nadroparin, Fraxiparine®, oprelvekin, Neumega®, pentosan polysulfate sodium, Elmiron®, reteplase, Retavase®, reviparin, Clivarine®, saruplase, streptokinase, Kabikinase®, Streptase®, tinzaparin, Innohep®, tirofiban, Aggrastat®, unfractionated heparin, low molecular weight heparin, all antithrombotic agents, all vitamin K antagonists, and all substances derived from and/or related to the foregoing substances.

21. A method for calculating a revised dose of Coumadin® for a patient using Coumadin®, comprising the steps of:
  accepting as a first input the patient's current Coumadin® dose;
  accepting as a second input a maximum dose of Coumadin®;
  accepting as a third input a percent response of the patient based on one or more surrogate markers for said patient; and
  determining a revised dose, wherein said revised dose is a function of said current dose minus a ratio of the percent response of the patient and a ratio of said current dose to said maximum dose plus the percent of individual patient response multiplied by a response factor.

22. The method of claim 21, wherein:
  said determining step includes determining said revised dose based on the equation $$RCD=CCD-\{[<(PCR-100)/PCR>/<1+(CCD/HIGH)>]\times CCD\}+LV$$

where:
  LV={(RESPONSE×CCD)×[(100−RES)×0.01]}1.3^(CCD/HIGH)
and wherein:
  RCD=Revised Coumadin® Dose
  CCD=Current Coumadin® Dose
  PCR=Percent response of patient to surrogate marker
  RES=Percent response of patient to last dosing based on surrogate marker
  HIGH=The input parameter that is the high dose range for Coumadin®
  RESPONSE=Percent of total dose available for individualizing patient dose
  1.3^(CCD/HIGH)=1.3 raised to an exponent (CCD/HIGH).

23. A method for calculating a revised dose of Coumadin® for a patient using Coumadin®, comprising the steps of:
  accepting as a first input the patient's current Coumadin® dose;
  accepting as a second input the maximum dose of Coumadin®;
  accepting as a third input one or more numerical markers indicating a response of the patient; and
  calculating said revised dose, wherein said revised dose is a function of said current dose minus the ratio of the change in numerical markers and the ratio of said current dose to said maximum dose plus the percent of individual patient response multiplied by a response factor.

24. The method of claim 23, wherein:
  said calculating step includes calculating said revised dose based on the equation $$RCD=CCD-\{[<(CCNM-DCNM)/CCNM>/<1+(CCD/HIGH)>]\times CCD\}+LV$$

where:
  LV={(RESPONSE×CCD)×[(1+D)−(1+E)]/abs (1+D)}/1.3^(CCD/HIGH)
  E=CCNM−PCNM
  D=DCNM−PCNM
and wherein:
  RCD=Revised Coumadin® Dose
  CCD=Current Coumadin® Dose
  CCNM=Current Coumadin® Numerical Marker
  DCNM=Desired Coumadin® Numerical Marker PCNM=Previous Coumadin® Numerical Marker
HIGH=The input parameter that is the high dose range for Coumadin®
RESPONSE=Percent of total dose available for individualizing patient dose
abs=The absolute value of
$1.3\wedge(CCD/HIGH)=1.3$ raised to an exponent of (CCD/HIGH).

25. A method for determining a dose of Coumadin® for a patient, comprising the steps of:
   administering an initial dose of Coumadin® to the patient;
   evaluating the patient to monitor and characterize one or more numerical surrogate markers;
   determining, based on said numerical surrogate markers, if a dose change for Coumadin® is necessary; and
   calculating a revised dose as a function of said current dose minus the ratio of a percent response of the patient and the ratio of said current dose to the maximum dose plus the percent of individual patient response multiplied by a response factor.

26. A method for determining a dose of Coumadin® for a patient, comprising the steps of:
   administering an initial dose of Coumadin® to the patient;
   examining the patient to monitor and characterize one or more numerical surrogate markers;
   determining if a dose change is necessary; and
   calculating a revised dose as a function of said current dose minus the ratio of the change in numerical markers and the ratio of said current dose to the maximum dose plus the percent of individual patient response multiplied by a response factor.

27. A method for calculating a revised dose of Coumadin® for a patient, comprising the steps of:
   accepting as input the patient's current Coumadin® dose;
   accepting as input the maximum dose of Coumadin®;
   accepting as input the percent response of the patient based on surrogate markers; and
   calculating a revised dose, wherein said revised dose is a function of said current dose, said maximum dose, and said percent response of the patient based on said surrogate markers.

28. A method for calculating a revised dose of Coumadin® for a patient, comprising the steps of:
   accepting as input a patient's current Coumadin® dose;
   accepting as input a maximum dose of Coumadin®;
   accepting as input the previous, current and desired values of one or more numerical markers indicating the response of the patient; and
   calculating a revised dose, wherein said revised dose is a function of said current dose, said maximum dose, and said previous, current and desired values of said numerical markers.

29. A storage device having stored thereon an ordered set of instructions which, when executed by a computer, performs a method comprising the steps of:
   accepting as input a patient's current Coumadin® dose;
   accepting as input a maximum dose of Coumadin®;
   accepting as input a percent response of a patient based on surrogate markers; and
   calculating a revised dose, wherein said revised dose is a function of said current dose minus the ratio of a percent response of the patient and the ratio of said current dose to said maximum dose plus the percent of individual patient response multiplied by a response factor.

30. A storage device having stored thereon an ordered set of instructions which, when executed by a computer, performs a method comprising the steps of:
   accepting as input the patient's current Coumadin® dose;
   accepting as input the maximum dose of Coumadin®;
   accepting as input one or more numerical markers indicating the response of the patient; and
   calculating a revised dose, wherein said revised dose is a function of said current dose minus the ratio of the change in numerical markers and the ratio of said current dose to said maximum dose plus the percent of individual patient response multiplied by a response factor.

31. An apparatus for calculating a revised dose of Coumadin® for a patient comprising:
   means for accepting as input one or more markers which indicate a patient's response to a dose of Coumadin®;
   means for accepting as input the patient's current Coumadin® dose;
   means for accepting as input the maximum dose of Coumadin®; and
   means for calculating a revised dose of Coumadin® as a function of said markers, said current Coumadin® dose, and said maximum Coumadin® doses.

32. The apparatus of claim 31, wherein:
   said markers are actual numerical markers.

33. The apparatus of claim 31, wherein:
   said markers are surrogate markers representing a percent response of the patient to Coumadin®.

34. The apparatus of claim 31, wherein:
   said revised dose is calculated by the equation:

$$RCD=CCD-\{[<(CCNM-DCNM)/CCNM>/<1+(CCD/HIGH)>]\times CCD\}+LV$$

where:
   $LV=\{(RESPONSE\times CCD)\times[(1+D)-(1+E)]/abs\ (1+D)\}/1.3\wedge(CCD/HIGH)$
   $E=CCNM-PCNM$
   $D=DCNM-PCNM$
and wherein:
   RCD=Revised Coumadin® Dose
   CCD=Current Coumadin® Dose
   CCNM=Current Coumadin® Numerical Marker
   DCNM=Desired Coumadin® Numerical Marker
   PCNM=Previous Coumadin® Numerical Marker
   HIGH=The input parameter that is the high dose range for Coumadin®
   RESPONSE=Percent of total dose available for individualizing patient dose
   abs=The absolute value of
   $1.3\wedge(CCD/HIGH)=1.3$ raised to an exponent of (CCD/HIGH).

35. The apparatus of claim 31, wherein:
   said revised dose is calculated by the equation:

$$RCD=CCD-\{[<(PCR-100)/PCR>/<1+(CCD/HIGH)>]\times CCD\}+LV$$

where:
   $LV=\{(RESPONSE\times CCD)\times[(100-RES)\times 0.01]\}/1.3\wedge(CCD/HIGH)$
and wherein:
   RCD=Revised Coumadin® Dose CCD=Current Coumadin® Dose PCR=Percent response of patient to surrogate marker RES=Percent response of patient to last dosing based on surrogate marker HIGH=The input parameter that is the high dose range for Coumadin®

RESPONSE=Percent of total dose available for individualizing patient dose 1.3^(CDD/HIGH)=1.3 raised to an exponent of (CD/HIGH).

36. A method for calculating a revised dose of warfarin or a substance containing warfarin for a patient using warfarin or said substance containing warfarin, comprising the steps of:

accepting as a first input the patient's current warfarin or said substance containing warfarin dose;

accepting as a second input a maximum dose of warfarin or said substance containing warfarin;

accepting as a third input a percent response of the patient based on one or more surrogate markers for said patient; and determining a revised dose, wherein said revised dose is a function of said current dose minus a ratio of the percent response of the patient and a ratio of said current dose to said maximum dose plus the percent of individual patient response multiplied by a response factor.

37. The method of claim 36, wherein:

said determining step includes determining said revised dose based on the equation $$RWD=CWD-\{[<(PWR-100)/PWR>/<1+(CWD/HIGH)>]\times CWD\}+LV$$

where:

$LV=\{(RESPONSE\times CWD)\times[(100-RES)\times 0.01]\}/1.3^{(CWD/HIGH)}$ and wherein:

RWD=Revised Warfarin or said substance containing warfarin Dose

CWD=Current Warfarin or a substance containing warfarin Dose

PWR=Percent response of patient to surrogate marker

RES=Percent response of patient to last dosing based on surrogate marker

HIGH=The input parameter that is the high dose range for warfarin or said substance containing warfarin RESPONSE=Percent of total dose available for individualizing patient dose abs=The absolute value of 1.3^(CWD/HIGH)=1.3 raised to an exponent of (CWD/HIGH).

38. A method for calculating a revised dose of warfarin or a substance containing warfarin for a patient using warfarin or said substance containing warfarin comprising the steps of:

accepting as a first input the patient's current warfarin or said substance containing warfarin dose;

accepting as a second input the maximum dose of warfarin or said substance containing warfarin;

accepting as a third input one or more numerical markers indicating a response of the patient; and calculating said revised dose, wherein said revised dose is a function of said current dose minus the ratio of the change in numerical markers and the ratio of said current dose to said maximum dose plus the percent of individual patient response multiplied by a response factor.

39. The method of claim 38, wherein:

said calculating step includes calculating said revised dose based on the equation $$RWD=CWD-\{[<(CWNM-DWNM)/CWNM>/<1+(CWD/HIGH)>]\times CWD\}+LV$$

where:

$LV=\{(RESPONSE\times CWD)\times[(1+D)-(1+E)]/abs\ (1+D)\}/1.3^{(CWD/HIGH)}$

E=CWNM−PWNM

D=DWNM−PWNM and wherein:

RWD=Revised Warfarin or said substance containing warfarin Dose

CWD=Current Warfarin or said substance containing warfarin Dose

CWNM=Current Warfarin or said substance containing warfarin Numerical Marker

DWNM=Desired Warfarin or said substance containing warfarin Numerical Marker

PWNM=Previous Warfarin or said substance containing warfarin Numerical Marker

HIGH=The input parameter that is the high dose range for warfarin or said substance containing warfarin RESPONSE=Percent of total dose available for individualizing patient dose abs=The absolute value of 1.3^(CWD/HIGH)=1.3 raised to an exponent of (CWD/HIGH).

40. A method for determining a dose of warfarin or a substance containing warfarin for a patient, comprising the steps of:

administering an initial dose of warfarin or said substance containing warfarin to the patient;

evaluating the patient to monitor and characterize one or more numerical surrogate markers;

determining, based on said numerical surrogate markers, if a dose change for warfarin or said substance containing warfarin is necessary; and calculating a revised dose as a function of said current dose minus the ratio of a percent response of the patient and the ratio of said current dose to the maximum dose plus the percent of individual patient response multiplied by a response factor.

41. A method for determining a dose of warfarin or a substance containing warfarin for a patient, comprising the steps of:

administering an initial dose of warfarin or said substance containing warfarin to the patient;

examining the patient to monitor and characterize one or more numerical surrogate markers;

determining if a dose change is necessary; and calculating a revised dose as a function of said current dose minus the ratio of the change in numerical markers and the ratio of said current dose to the maximum dose plus the percent of individual patient response multiplied by a response factor.

42. A method for calculating a revised dose of warfarin or a substance containing warfarin for a patient, comprising the steps of:

accepting as input the patient's current warfarin or said substance containing warfarin dose;

accepting as input the maximum dose of warfarin or said substance containing warfarin;

accepting as input the percent response of the patient based on surrogate markers; and calculating a revised dose, wherein said revised dose is a function of said current dose, said maximum dose, and said percent response of the patient based on said surrogate markers.

43. A method for calculating a revised dose of warfarin or a substance containing warfarin for a patient, comprising the steps of:
   accepting as input a patient's current warfarin or said substance containing warfarin dose;
   accepting as input a maximum dose of warfarin or said substance containing warfarin;
   accepting as input the previous, current and desired values of one or more numerical markers indicating the response of the patient; and
   calculating a revised dose, wherein said revised dose is a function of said current dose, said maximum dose, and said previous, current and desired values of said numerical markers.

44. A storage device having stored thereon an ordered set of instructions which, when executed by a computer, performs a method comprising the steps of:
   accepting as input a patient's current warfarin or a substance containing warfarin dose;
   accepting as input a maximum dose of warfarin or said substance containing warfarin;
   accepting as input a percent response of a patient based on surrogate markers; and
   calculating a revised dose, wherein said revised dose is a function of said current dose minus the ratio of a percent response of the patient and the ratio of said current dose to said maximum dose plus the percent of individual patient response multiplied by a response factor.

45. A storage device having stored thereon an ordered set of instructions which, when executed by a computer, performs a method comprising the steps of:
   accepting as input the patient's current warfarin or a substance containing warfarin dose;
   accepting as input the maximum dose of warfarin or said substance containing warfarin;
   accepting as input one or more numerical markers indicating the response of the patient; and
   calculating a revised dose, wherein said revised dose is a function of said current dose minus the ratio of the change in numerical markers and the ratio of said current dose to said maximum dose plus the percent of individual patient response multiplied by a response factor.

46. An apparatus for calculating a revised dose of warfarin or a substance containing warfarin for a patient, comprising:
   means for accepting as input one or more markers which indicate a patient's response to a dose of warfarin or said substance containing warfarin;
   means for accepting as input the patient's current warfarin or said substance containing warfarin dose;
   means for accepting as input the maximum dose of warfarin or said substance containing warfarin; and
   means for calculating a revised dose of warfarin or said substance containing warfarin as a function of said markers, said current warfarin or said substance containing warfarin dose, and said maximum warfarin or said substance containing warfarin dose.

47. The apparatus of claim 46, wherein:
   said markers are actual numerical markers.

48. The apparatus of claim 46, wherein:
   said markers are surrogate markers representing a percent response of the patient to warfarin or said substance containing warfarin.

49. The apparatus of claim 46, wherein:
   said revised dose is calculated by the equation:

$$RWD = CWD\{[<(CWNM-DWNM)/CWNK>/<1+(CWD/HIGH))]\times CWD\} + LV$$

where:

$LV = \{(RESPONSE \times CWD) \times [(1+D)-(1+E)]/abs\ (1+D)\}/1.3^{\wedge}(CWD/HIGH)$ $E = CWNM - PWNM$ $D = DWNM - PWNM$ and wherein:
   RWD=Revised Warfarin or said substance containing warfarin Dose
   CWD=Current Warfarin or said substance containing warfarin Dose
   CWNM=Current Warfarin or said substance containing warfarin Numerical Marker
   DWNM=Desired Warfarin or said substance containing warfarin Numerical Marker
   PWNM=Previous Warfarin or said substance containing warfarin Numerical Marker
   HIGH=The input parameter that is the high dose range for warfarin or said substance containing warfarin
   RESPONSE=Percent of total dose available for individualizing patient dose
   abs=The absolute value of
   $1.3^{\wedge}CWD/HIGH)=1.3$ raised to an exponent of (CWD/HIGH).

50. The apparatus of claim 46, wherein:
   said revised dose is calculated by the equation:

$$RWD = CWD\{[<(PWR-100)/PWR>/<1+(CWD/HIGH)>]\times CWD\} + LV$$

where:

$LV = \{(RESPONSE \times CWD) \times [(100-RES) \times 0.01]\}/1.3^{\wedge}(CWD/HIGH)$ and wherein:
   RWD=Revised Warfarin or said substance containing warfarin Dose
   CWD=Current Warfarin or said substance containing warfarin Dose
   PWR=Percent response of patient to surrogate marker
   RES=Percent response of patient to last dosing based on surrogate marker
   HIGH=The input parameter that is the high dose range for warfarin or said substance containing warfarin
   RESPONSE=Percent of total dose available for individualizing patient dose
   abs=The absolute value of
   $1.3^{\wedge}(CWD/HIGH)=1.3$ raised to an exponent of (CWD/HIGH).

* * * * *

UNITED STATES PATENT AND TRADEMARK OFFICE
CERTIFICATE OF CORRECTION

PATENT NO. : 6,942,614 B1
DATED : September 13, 2005
INVENTOR(S) : John D. Kutzko, Michael G. Singer and John McMichael It is certified that error appears in the above-identified patent and that said Letters Patent is hereby corrected as shown below:

Column 1,
Line 10, replace "1999 now" with -- 1999, now --.
Line 57, replace "thattaking" with -- that taking --.

Column 4,
Line 49, replace "CurrentAnticoagulant" with -- Current Anticoagulant --.

Column 6,
Line 15, replace "RAD=CAD-{[<(CANM-DANM)/CANM>l<1+(CAD/HIGH)>] 33 CAD}+LV" with -- RAD=CAD-{[<(CANM-DANM)/CANM>/<1+(CAD/HIGH)>XCAD}+LV --.

Column 8,
Line 67, replace "/HIGH)<]" with -- /HIGH)>] --.

Column 16,
Line 10, replace "/CWNK>" with -- /CWNM> --.
Line 10, replace "HIGH))]" with -- /HIGH)>] --.
Line 40, replace "CWD}" with -- CWD-{ --.

Signed and Sealed this

Sixth Day of June, 2006

JON W. DUDAS
*Director of the United States Patent and Trademark Office*